(12) United States Patent
Wald et al.

(10) Patent No.: US 12,270,872 B2
(45) Date of Patent: Apr. 8, 2025

(54) ASYMMETRIC SINGLE-CHANNEL RADIO FREQUENCY HELMET COIL FOR MAGNETIC RESONANCE IMAGING

(71) Applicant: The General Hospital Corporation, Boston, MA (US)

(72) Inventors: Lawrence L. Wald, Cambridge, MA (US); Clarissa Zimmerman-Cooley, Boston, MA (US); Patrick C. McDaniel, Boston, MA (US); Sai Abitha Srinivas, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 204 days.

(21) Appl. No.: 17/996,857

(22) PCT Filed: Apr. 26, 2021

(86) PCT No.: PCT/US2021/029175
§ 371 (c)(1),
(2) Date: Oct. 21, 2022

(87) PCT Pub. No.: WO2021/217137
PCT Pub. Date: Oct. 28, 2021

(65) Prior Publication Data
US 2023/0144076 A1 May 11, 2023

Related U.S. Application Data

(60) Provisional application No. 63/015,172, filed on Apr. 24, 2020.

(51) Int. Cl.
*A61B 5/055* (2006.01)
*A61B 5/00* (2006.01)
*G01R 33/34* (2006.01)

(52) U.S. Cl.
CPC ........ *G01R 33/34084* (2013.01); *A61B 5/055* (2013.01); *A61B 5/6803* (2013.01); *G01R 33/34007* (2013.01)

(58) Field of Classification Search
CPC .................. A61B 5/055; A61B 5/6803; G01R 33/34007; G01R 33/34046; G01R 33/34084
See application file for complete search history.

(56) References Cited

U.S. PATENT DOCUMENTS

| | | |
|---|---|---|
| 2005/0107686 A1 | 5/2005 | Chan et al. |
| 2008/0007259 A1 | 1/2008 | Driemel |
| 2013/0076358 A1 | 3/2013 | Taracila et al. |

(Continued)

OTHER PUBLICATIONS

International Search Report in PCT/US2021/029175; received on Aug. 5, 2021.

*Primary Examiner* — Mark D Remaly
(74) *Attorney, Agent, or Firm* — QUARLES & BRADY LLP

(57) ABSTRACT

Asymmetric, single-channel radio frequency ("RF") coils are provided for use with portable or other low-field magnetic resonance imaging ("MRI") systems. In general, the asymmetric, single-channel RF coils make use of asymmetric, optimized winding configurations in order to reduce B1+ inhomogeneities and to reduce signal sensitivity outside of the desired imaging field-of-view ("FOV").

20 Claims, 12 Drawing Sheets

(56) References Cited

U.S. PATENT DOCUMENTS

2016/0349336 A1   12/2016  Chang et al.
2017/0010339 A1*  1/2017  Rosen .............. G01R 33/34084
2019/0353735 A1   11/2019  Yang

* cited by examiner

ASYMMETRIC SINGLE-CHANNEL RADIO FREQUENCY HELMET COIL FOR MAGNETIC RESONANCE IMAGING

CROSS-REFERENCE TO RELATED APPLICATIONS

This application represents the U.S. national stage entry of International Application No. PCT/US2021/029175 filed Apr. 26, 2021, which is based on and claims the benefit of U.S. Provisional Patent Application Ser. No. 63/015,172 filed on Apr. 24, 2020 and entitled "ASYMMETRIC SINGLE-CHANNEL HELMET COIL FOR HEAD-ONLY PORTABLE MRI." The contents of these applications are incorporated herein by reference in their entirety.

STATEMENT REGARDING FEDERALLY SPONSORED RESEARCH

This invention was made with government support under EB018976 awarded by the National Institutes of Health. The government has certain rights in the invention.

BACKGROUND

Access to magnetic resonance imaging ("MRI") is limited by cost, size, and siting requirements. Specialized portable systems could increase accessibility and enable point-of-care ("POC") MRI. Portable MRI scanners have been designed for extremity imaging, single-sided imaging, and brain imaging. These systems leverage the anatomy of the target to greatly reduce the size and weight of the hardware and reduce the required imaging field-of-view ("FOV").

In the pursuit of portability, the real estate inside the main magnet bore is limited. Therefore, it is desirable to use tight-fitting radio frequency ("RF") coils, which also has positive implications for power efficiency and imaging sensitivity. The most efficient configuration is a joint transmit-receive RF coil. In the case of human brain imaging, this may take the form of a single-channel transmit-receive RF coil helmet.

However, when the windings are uniformly distributed on the helmet former problems can result. As one example, the B1+ can be inhomogeneous, causing flip-angle variations in the FOV and imaging artifacts. As another example, the B1+ and B1− fields can extend into regions that aren't encoded for imaging (e.g., the un-encoded lower part of the head/neck in brain imaging applications), resulting in undesirable signal pick-up that aliases back into the images.

SUMMARY OF THE DISCLOSURE

The present disclosure addresses the aforementioned drawbacks by providing a radio frequency (RF) coil system for performing a magnetic resonance imaging (MRI) process using an MRI system. The RF coil system includes a substrate configured to follow a contour of a portion of a subject to be imaged by the MRI system and at least one RF coil coupled to the substrate. The at least one RF coil forms an asymmetrical three-dimensional spiral pattern extending over the substrate, wherein the asymmetrical three-dimensional spiral pattern includes adjacent portions of the at least one RF coil that are non-uniformly spaced apart over the substrate.

It is another aspect of the present disclosure to provide a single channel radio frequency (RF) coil configured for a portion of human anatomy. The single channel RF coil includes a conductor arranged in a three-dimensional asymmetrical geometry about a region-of-interest. When the single channel RF coil is operated in conjunction with performing magnetic resonance of the portion of the human anatomy of a subject, the conductor is configured to produce and detect magnetic fields substantially parallel to a longitudinal axis of the subject's body.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 6A is an example RF coil design surface shown in relation to a head-shaped ROI, where some ROI points sit outside of the RF coil design surface. FIG. 6B is an RF coil design surface shown with modified "uniform" and "null" ROIs.

FIG. 7A shows optimized RF coil designs that produce x-polarized and y-polarized B1 field. FIG. 7B shows simulated spatial maps of the transverse ($B_{1,xy}$) field component for the two coils shown in FIG. 7A. FIG. 7C shows field histograms for the "uniform" and "null" ROIs for the two coil designs shown in FIG. 7A.

FIG. 9A shows a CAD rendering of the RF coil former tiles with optimized wire grooves. FIG. 9B shows the 3D-printed coil former tiles. FIG. 9C shows the assembled coil former without coil windings. FIG. 9D shows the assembled coil former with coil windings in an isometric view. FIG. 9E shows the assembled coil former with coil windings in a side view (i.e., XZ plane view). FIG. 9F shows the assembled coil showing the tune/match/feed board.

DETAILED DESCRIPTION

Described here are asymmetric, single-channel radio frequency ("RF") coils for use with portable or other low-field magnetic resonance imaging ("MRI") systems, and methods for the design and construction of such RF coils. In general, the RF coils described in the present disclosure make use of asymmetric, optimized winding configurations in order to reduce B1+ inhomogeneities and to reduce signal sensitivity outside of the desired imaging field-of-view ("FOV").

The RF coils described in the present disclosure can be integrated into a former that is shaped for the particular anatomy under consideration. For instance, an RF coil can be a single-channel RF coil helmet for use with a portable brain MRI scanner. The single-channel coils can be designed on a helmet former, such as a tight-fitting helmet former, with wire patterns that improve B1+ uniformity within the imaging region-of-interest ("ROI") and reduce signal sensitivity outside of the imaging ROI.

As one example, the RF coil can include a coil design that uses a solenoid-like spiral pattern with a variable turn density along the craniocaudal direction (i.e., the head-foot direction). The total length of the spiral in the craniocaudal direction can be relatively short in order to reduce the MR sensitivity in the lower head and neck area. For example, the total length of the spiral can be on the order of 10.7 cm. When compared to a uniform winding distribution, the variable turn density can reduce the B1+ range by around 80% within the ROI.

As another example, the RF coil can include a coil design that uses a wire pattern that produces a transverse field (i.e., orthogonal to the $B_0$ field of the MRI system), which naturally reduces the RF coil's sensitivity outside of the imaging ROI (e.g., in the lower head and neck). The winding pattern in these instances can be optimized using a boundary element method ("BEM") stream-function method with a homogeneous target field in the ROI and a target field of zero in a region adjacent the ROI (e.g., the lower head/neck area).

In some low-field MRI systems, the magnet system can be constructed using a bi-planar configuration for the $B_0$ magnet. In these instances, the $B_0$ magnet includes coils in opposing parallel planes that are spaced apart by a distance. When operated, the coils produce a $B_0$ field that is oriented in a direction transverse to the planes of the coils. When a subject is placed between the coils (e.g., in a supine position), the $B_0$ field is perpendicular to the longitudinal axis of the body of the subject. Accordingly, portable or low-field MRI systems having a $B_0$ field oriented in this manner can be used with RF coils designed using the geometries described in the present disclosure.

Figure 1A:
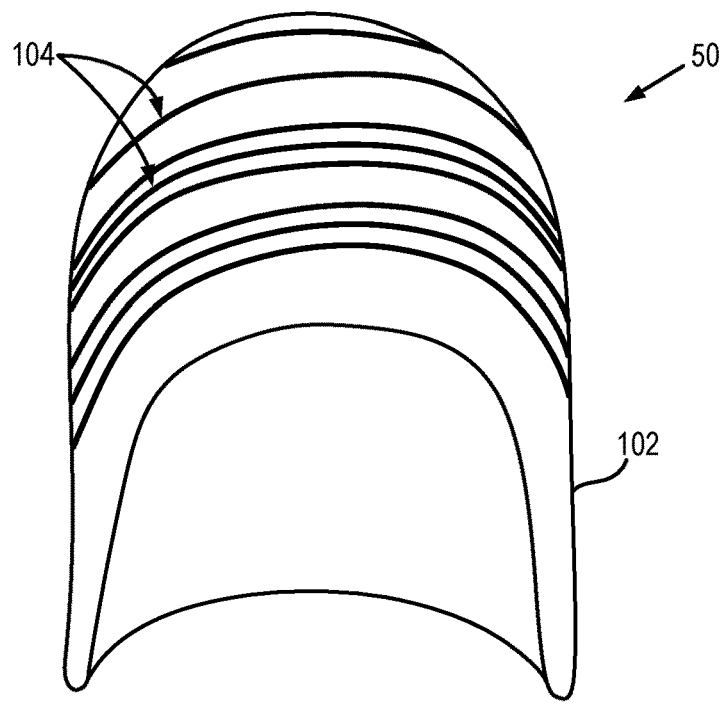
FIGS. 1A-1C show an example transmit/receive coil having asymmetric coil windings in accordance with some embodiments described in the present disclosure.
Figure 1B:
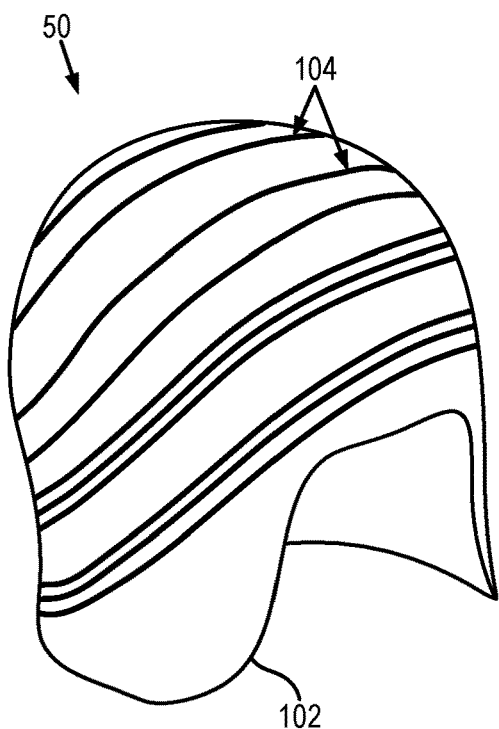
Figure 1C:
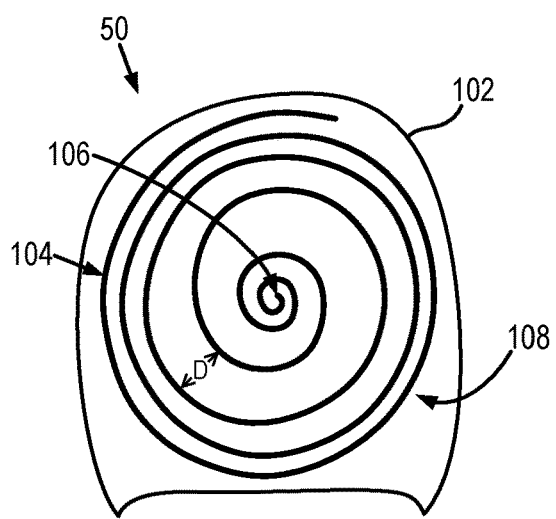

Referring to FIGS. 1A-1C, a transmit/receive RF coil design, illustrated as an asymmetric RF coil 50, is illustrated. As will be described, the asymmetric RF coil 50 provides a homogeneous magnetic field and high sensitivity over three-dimensional volumes, while also achieving a reduced sensitivity in regions outside of the desired imaging FOV. The asymmetric RF coil 50 includes a substrate 102 to which, or on which, a coil 104 is coupled. The substrate 102 may be highly form fitting. For example, the substrate 102 may be a former created using three-dimensional ("3D") printing to specifically contour to anatomy, such as a head. Thus, the substrate 102 may be formed of a material suitable for 3D printing. Likewise, the windings of the coil 104 may be tailored to comfortably fit the underlying anatomy.

The coil 104, as illustrated, forms an asymmetric spiral (e.g., a spiral with a variable turn density). The coil 104 may spiral out from a center 106 aligned with a crown of the head of the subject to a perimeter 108 encircling the head of the subject. Thus, the coil 104 may be configured to spiral out from the center 106 to the perimeter 108. The coil 104 may be arranged to have a non-uniform distance (D) between adjacent portions of the spiral. In any case, the coil 104 forms a hemispherical spiral pattern that provides high magnetic field homogeneity. The spiral pattern advantageously controls or removes the need for coil decoupling strategies common in many transmit/receive coils. As opposed to conventional surface coils that provide high sensitivity, but suffer from high magnetic field inhomogeneity and need a separate coil for transmit operations, the above-described spiral coil of the present disclosure can be tuned to provide high homogeneity, while maintaining high sensitivity over large FOVs in a streamlined design. The asymmetric RF coil 50 can be used for both transmit and receive operations.

Figure 2A:
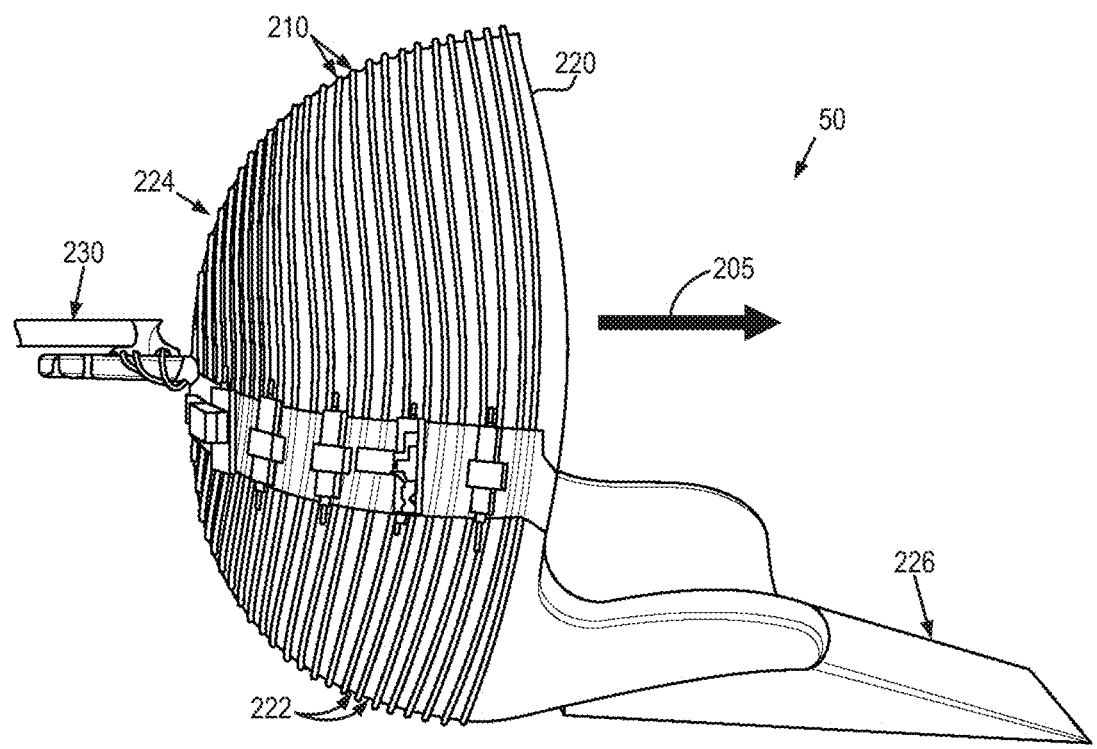
FIGS. 2A and 2B show an example radio frequency ("RF") coil having an asymmetric three-dimensional spiral configuration coupled to a helmet for use in imaging a subject's head with a portable and/or low-field magnetic resonance imaging ("MRI") system.
Figure 2B:
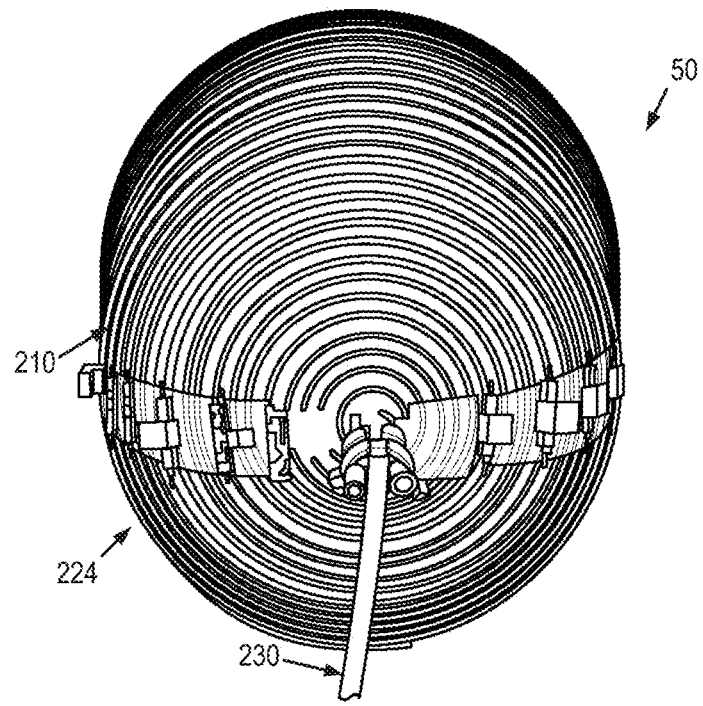

FIGS. 2A and 2B illustrate another design for an asymmetric RF coil for use with imaging the head in a portable MRI or low-field MRI system. The asymmetric RF coil 50 includes a substrate 220 formed to accommodate the head of a subject to be imaged. The substrate may be formed with grooves 222 in which conductor 210 is provided (e.g., wound) according to a desired geometry. The substrate 220 may be, for example, designed via computer assisted design ("CAD") and then produced using 3D printing or other additive manufacturing techniques, or the substrate 220 may be formed using any other suitable manufacturing technique. The substrate 220 includes a helmet portion 224 to accommodate the head and a support base 226 so that a patient can comfortably rest the head within the helmet portion 224 while in a supine position. An electrical connector 230 provides a connection between the RF coil 50 and the RF subsystem of the MRI system.

As illustrated, the conductor 210 is wound about the substrate 220 in an asymmetric spiral geometry so that, when operated, the coil 50 produces a magnetic field in the direction indicated by arrow 205, and can detect magnetic fields oriented in the same direction. According to some embodiments, the conductor 210 can include a single continuous wire forming a single-channel transmit/receive RF coil. In some embodiments, the conductor 210 can be a single stranded wire of appropriate gauge. In some other embodiments, the conductor 210 can be a multi-stranded wire, such as a Litz wire. A Litz wire is a bundle of individually insulated wire conductors that are bundled, twisted, or woven together.

Advantageously, using a Litz wire can produce an RF coil having the same inductance as a single-stranded wire of the same gauge, but having a fraction of the resistance at the operating frequencies characteristic of portable MRI and/or low-field MRI. As a result, resistive losses are substantially reduced, thereby decreasing the noise of the transmit/receive coil and increasing signal-to-noise ratio ("SNR").

As a non-limiting example, an RF coil can be constructed based on a compact spiral helmet design and used for transmit and receive with a passive transmit-receive switch. The coil can be wound on a tightly fitting helmet former of inner dimensions: 21 cm (anterior-posterior), 17 cm (medial-lateral). The windings can extend 10.7 cm from the top of the head. The close-fitting, asymmetrical spiral pattern provides favorable RF receive efficiency and sensitivity.

To improve the B1+ homogeneity, the winding distribution can be designed using a BEM stream-function based method and/or adjusted using Biot-Savart simulations. As a non-limiting example, the coil may have a winding distribution that results in a total of 12 asymmetric windings with a higher turn-density near the bottom of the coil, similar to the example shown in FIGS. 2A and 2B. As described above, the coil can be constructed on a 3D printed polycarbonate former with winding grooves. As also described above, the non-uniform turn distribution can be wound with Litz wire (e.g., AWG 20 5/39/42, New England Wire, Lisbon, N.H.). In one example implementation, the RF coil can be tuned and matched with nonmagnetic capacitors to 50 ohms for a portable MRI system's 3.39 MHz Larmor frequency.

As described above, in some embodiments, a BEM based method can be sued to design the winding distribution in the asymmetric RF coils described in the present disclosure. In a BEM approach to coil design, any surface on which electrical current can flow can be approximated or represented by a collection of triangular elements that form a mesh over the whole surface. The vertices of the triangular elements in the mesh are referred to as nodes. Within each element is contained information that describes the direction and magnitude of the electrical current density. To design an RF coil using BEM-based techniques, a surface geometry is discretized into a finite mesh composed of finite elements, which may be triangular elements or other shaped elements.

In practice, the current density pattern over a two-dimensional surface can be represented in an indirect manner in the form of a scalar stream function. The stream function can be represented as a piece-wise linear (or higher order) function over the surface geometry on which the gradient coils are to be placed. The stream function can include a single scalar value for each node in the mesh, and when all of the nodes are considered together, the stream function can be transformed to find the direction and magnitude of the current density in each triangular element.

In one implementation, a stream function, $\psi(r)$, residing within the surface of elements with corresponding current density, $J(r)$, can be defined, where r represents the position on the mesh. The stream function can be approximated by a weighted sum of basis functions for each node, n, as:

$$\psi(r) = \sum_{n=1}^{N} I_n \psi_n(r); \quad (1)$$

where $I_n$ is a weighting coefficient for the basis function, $\psi_n(r)$, of the $n^{th}$ node. With this approximation, the current density for the stream function can be represented as a sum of current density basis functions, which can be defined as, $$J(r) = \nabla \times (\psi(r)n(r)); \quad (2)$$

$$J(r) \approx \sum_{n=1}^{N} I_n \nabla \times (\psi_n(r)n(r)); \quad (3)$$

$$J(r) \approx \sum_{n=1}^{N} I_n J_n(r); \quad (4)$$

$$J_n(r) \approx \sum_{k=1}^{K} v_{nk} = \sum_{k=1}^{K} \frac{e_{nk}}{2A_k}; \quad (5)$$

where n(r) is the outward point normal of the surface; K is the number of triangles surrounding the node, n; $A_k$ is the area of triangular element, k, associated with node, n; and $e_{nk}$ is the vector that opposes node n with triangular element, k.

The current density representation, or the stream functions, can be used to produce a pattern of current density that achieves the set requirements for one or more performance metrics. As one non-limiting example, the current density representation, or the stream functions, can be used to produce a pattern of current density that balances achieving a homogeneous target field in a specified imaging ROI (e.g., the brain) and a target field of zero in a region adjacent the specified imaging ROI (e.g., the lower head/neck area).

Figure 3:
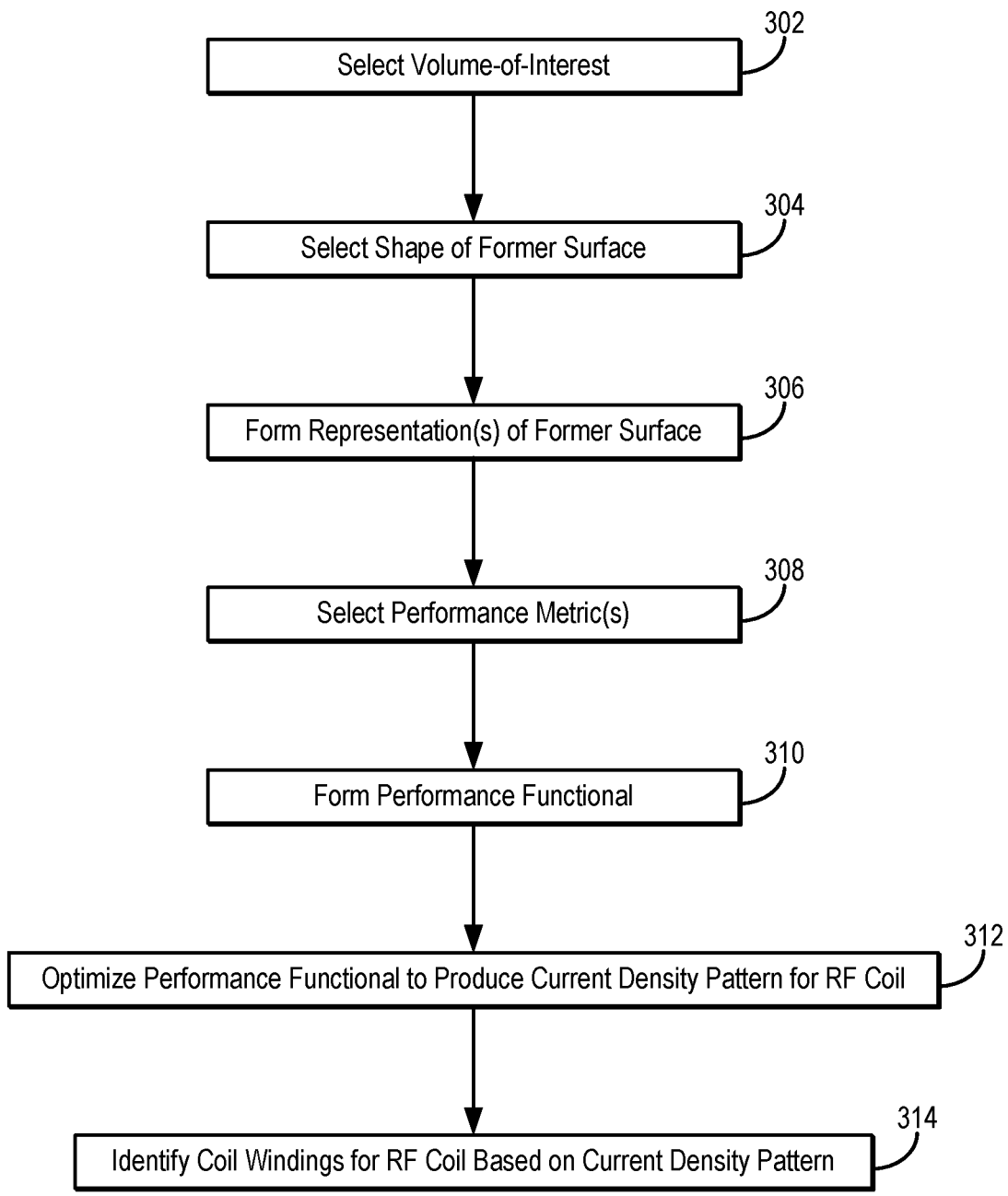
FIG. 3 is a flowchart setting forth the steps of an example method for designing an asymmetrical RF coil according to some embodiments described in the present disclosure.

Referring now to FIG. 3, a flowchart is illustrated as setting forth the steps of an example of a method for designing, and constructing, an asymmetrical RF coil according to some embodiments described in the present disclosure.

The method includes selecting a volume-of-interest in which the B1+ field will be generated, as indicated at step 302. As one example, the volume-of-interest is selected to correspond with a volume within the former onto which the RF coil windings will be coupled.

The shape of the surface on which the RF coil will be constructed is next selected, as indicated at step 304. As one example, the shape of this surface may be the shape of the former and/or helmet for which the RF coil is being designed. One or more representations of the selected surface are then formed, as indicated at step 306. As described above, this step can include forming a mesh representation of the selected surface. As one example, the mesh can include a triangulated mesh that is composed of triangular elements.

One or more performance metrics for the design of the RF coil are then selected and set, as indicated at step 308. For example, the B1+ homogeneity within the specified volume-of-interest can be selected, as can the target field strength within and outside of the volume-of-interest.

To find the stream function and corresponding current density representation that achieves the specified requirements set for the RF coil design, a performance functional is formed based at least in part on the set performance metrics, as indicated at step 310. The performance functional can be, for instance, a cost function including one or more terms associated with the performance metrics. In some implementations, the performance metrics can be implemented in the performance functional as weighting parameters. In other implementations, the performance metrics can be implemented in the performance functional as constraints set on the performance functional. A constraint can be set in the form of a single value (i.e., constrained to zero) or a range of values that are acceptable for that performance metric. The approaches for implementing the performance metrics can also be combined. For instance, some performance metrics can be used to constrain the performance functional and other performance metrics can be implemented as weighting parameters in the performance functional.

Once the performance functional is formed, it can be minimized or optimized to produce a current density pattern that achieves the specified RF coil performance metric constraints, as indicated at step 312. The minimization can be based on various techniques such as least-squares matrix inversion, analytic formulae or an iterative solver.

For example, where one or more performance metrics are set as weighting parameters, competing performance metrics can be simultaneously balanced to achieve the desired performance metric requirements by finding a set of parameters that minimizes the performance functional. As another example, where one or more performance metrics are set as constraints, a constrained optimization can be used to find the desired performance metric requirements.

In some implementations, the solution of the performance functional itself can be constrained to a certain desired range. If the solution is not within this desired range, then performance metrics or weighting parameters can be changed, for example, to obtain a different solution. This process can be iteratively repeated until the solution is within the range of acceptable design goals. Example design goals can include minimum conductor separation, maximum power deposition per unit area, maximum force on a given component, and so on.

Coil windings for the RF coil are then identified based on the minimized performance functional, as indicated at step 316. For instance, current density can be computed based on the minimized performance functional and coil windings can be determined based on the computed current density.

For instance, the current density pattern obtained by minimizing or optimizing the performance functional can be contoured to obtain a wire pattern, which is a discrete number of current paths that approximates the current density represented by the stream function. The choice of number of contours (and thus the coil wire density) can also be based on the performance metric weightings and constraints since some of the performance metric weightings and constraints may be related to wire density, for example, a constraint to enforce a certain minimum wire separation or a specified spiral turn density.

Figure 4A:
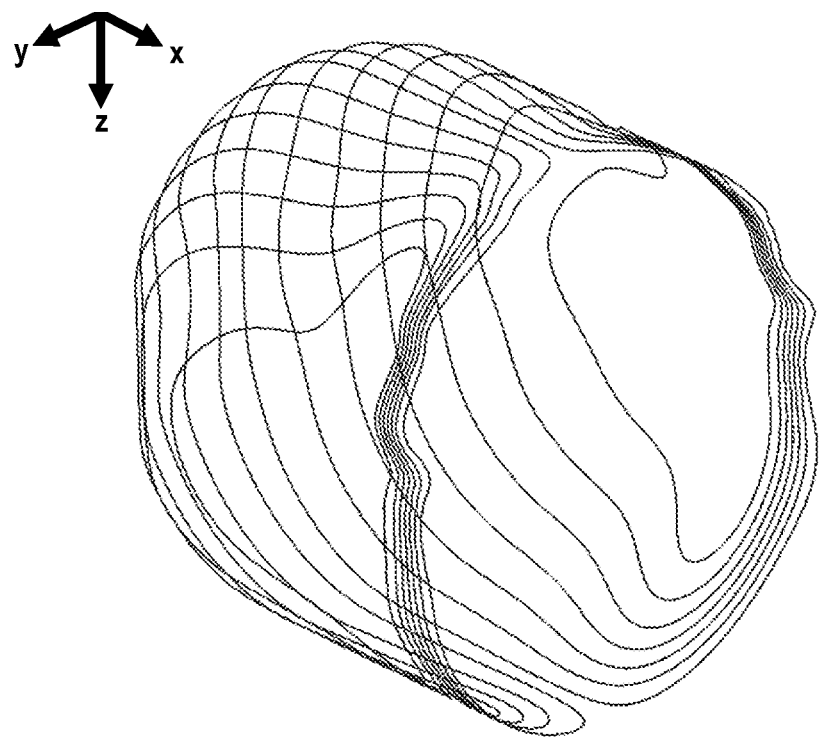
FIGS. 4A and 4B show examples of optimized coil windings computed using a BEM stream function technique.
Figure 4B:
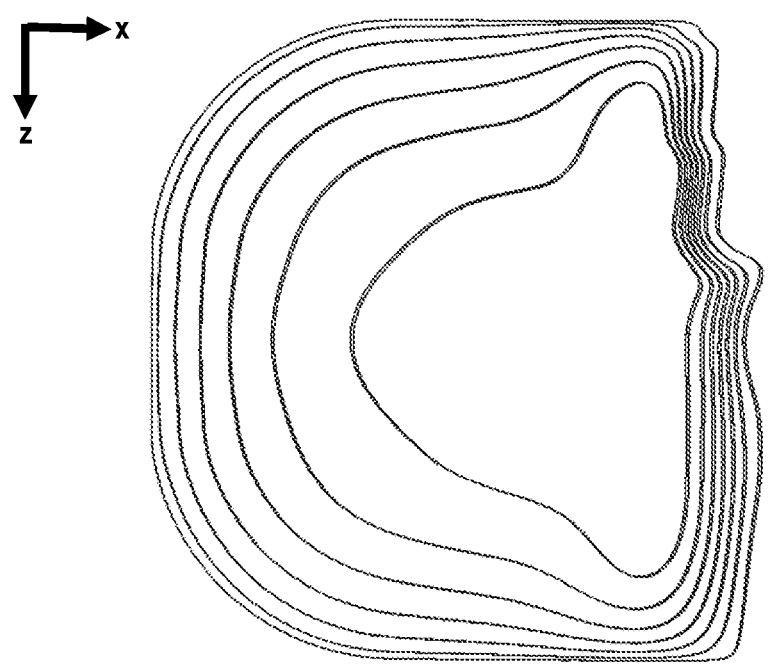
Figure 5A:
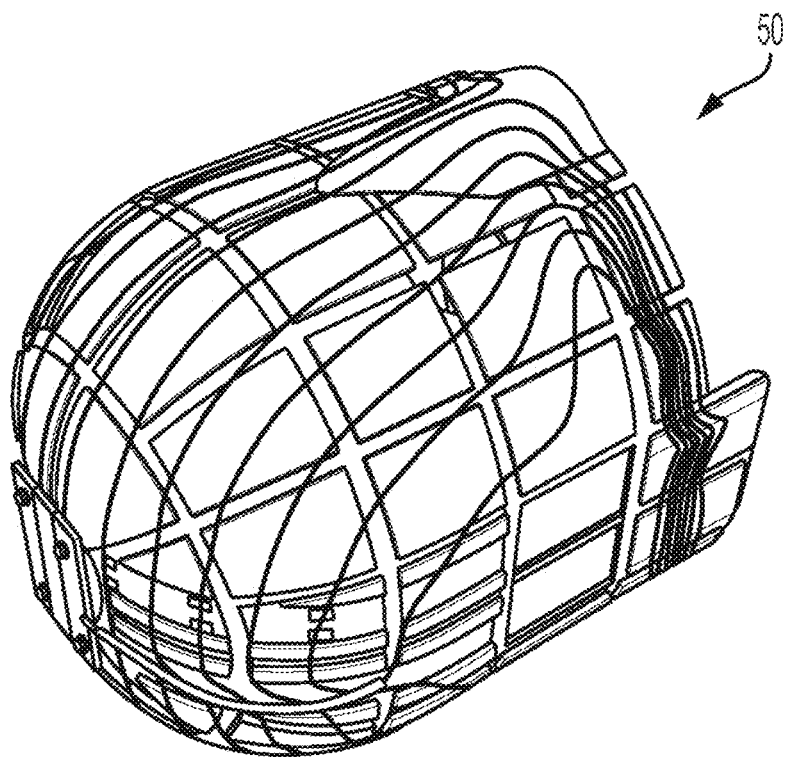
FIGS. 5A and 5B show views of an example transverse transmit/receive RF coil constructed using the optimized coil windings shown in FIGS. 4A and 4B, where the transverse transmit/receive RF coil has an asymmetric three-dimensional geometry about a region-of-interest.
Figure 5B:
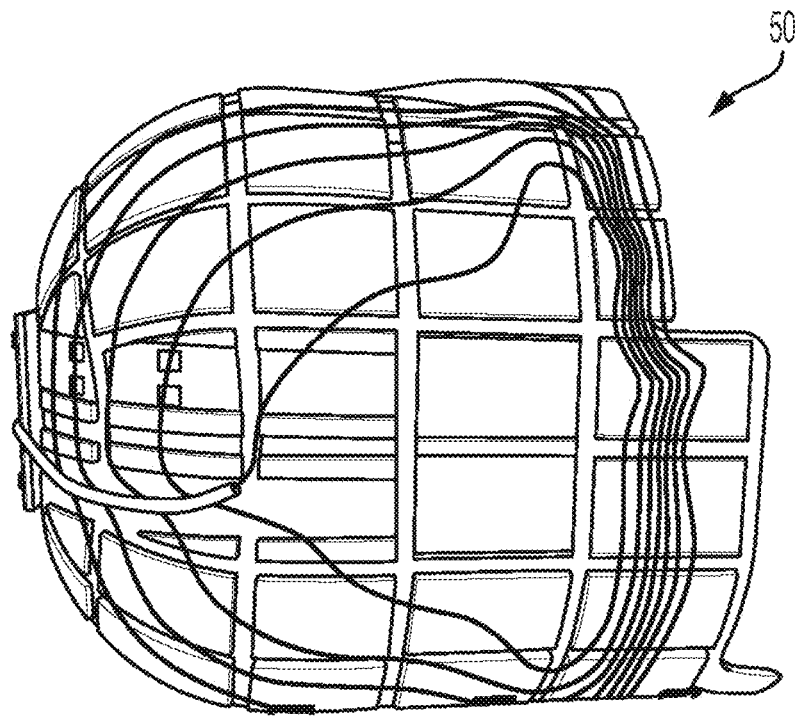

FIGS. 4A and 4B show an example of optimized coil winding patterns generated using the methods described in the present disclosure, and FIGS. 5A and 5B show example views of a transverse transmit/receive RF coil 50 manufactured using those optimized coil winding patterns. In particular, the example coil winding patterns shown in FIGS. 4A and 4B were generated using a BEM stream function method in which the optimization target was set to include a uniform B1 field in a brain region while having a zero B1 field in the neck region of a patient. As described above, the zero B1 field target in the neck region was set in order to prevent image artifacts from signal fold-in from the neck, which are not encoded by the gradient coils of the MRI system. As described herein, the transverse transmit/receive RF coil 50 shown in FIGS. 5A and 5B is a single-channel, asymmetric RF coil 50 suitable for use with a portable MRI system or other low-field MRI system.

The RF coils manufactured and operated in accordance with the above described methods can be applied to any application or geometry of MRI systems. The above-described asymmetric RF coil 50, and other asymmetric RF coils designed for use with other anatomy or differently shaped regions-of-interest, can be used for MRI of human body parts, like the head, arm, leg, hand, or any extremities to provide high sensitivity with any type of MRI sequence including gradient-echo based sequences, spin-echo based sequences, and fully-refocused sequences.

Advantageously, the asymmetric RF coils described in the present disclosure can be used with portable MRI systems, or other low-field MRI systems. For example, portable MRI may be advantageous for point-of-care imaging applications. Likewise, low-field MRI may be advantageous for imaging subjects who may otherwise be excluded from conventional MRI due to metal implants, pacemakers, and the like.

In one example, a low-field MRI system utilizes much of the same hardware as a conventional MRI system, but can have substantially reduced hardware requirements and a smaller hardware footprint relative to those conventional MRI systems. Low-field MRI systems generally operate at magnetic field strengths of 0.2 T and below. As a non-limiting example, the magnetic field used in a portable and/or low-field MRI system may be between 5 mT and 0.2 T. For example, the magnetic field may between 5 mT and 100 mT. Non-limiting examples of field strengths in this range include 80 mT, 10 mT, 6.5 mT, and so on.

Figure 6A:
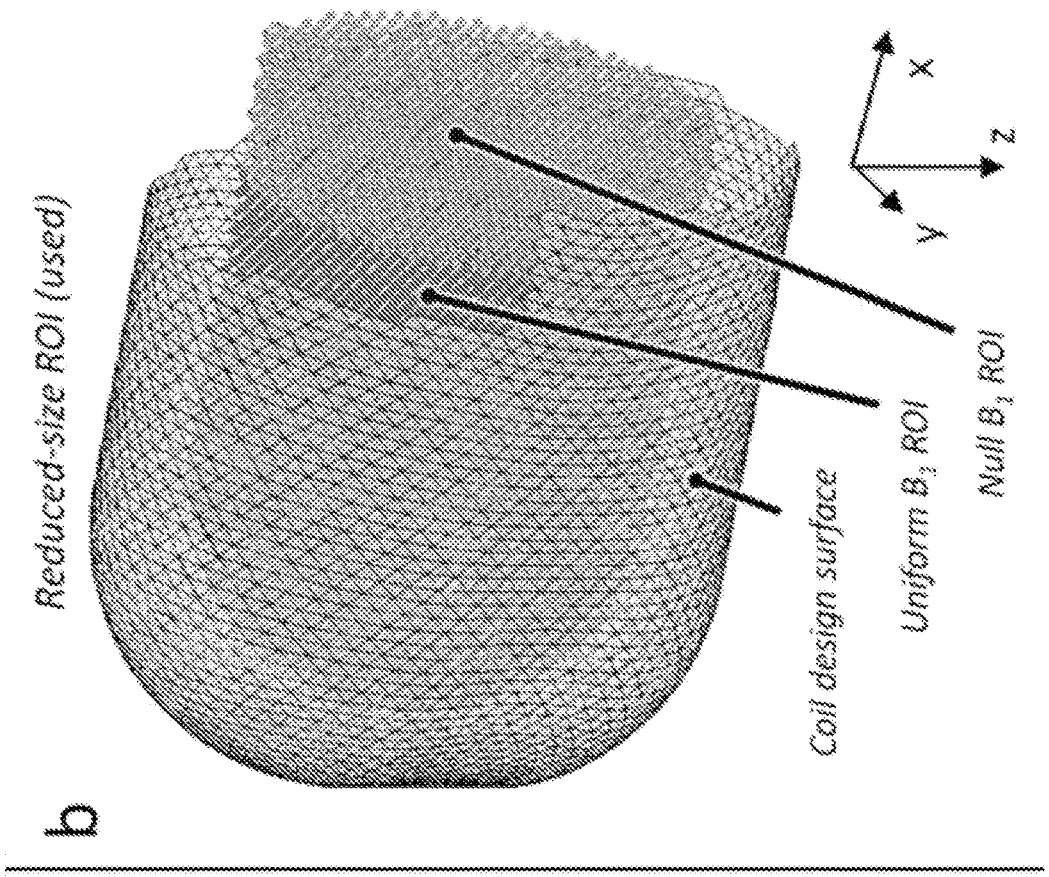
FIGS. 6A and 6B show examples of RF coil design surfaces.
Figure 6B:
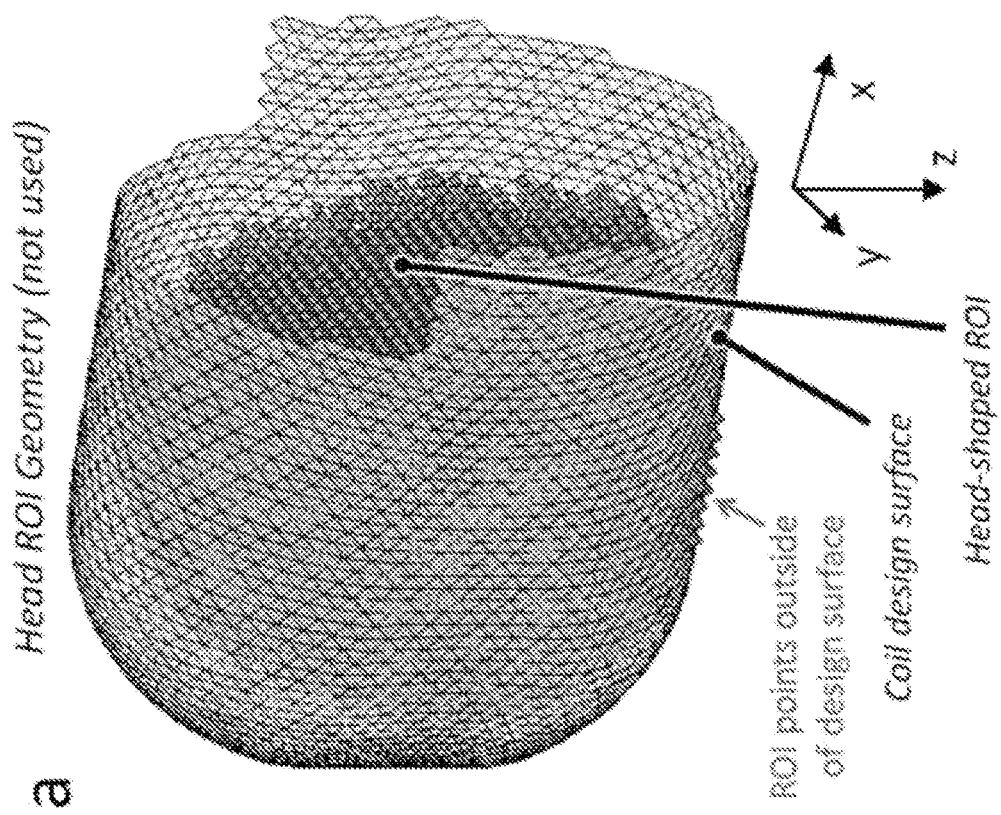

As a non-limiting example, an RF coil was designed for transmit and receive on a helmet-shaped surface that is close to the patient's head. The coil design optimization used a target ROI that was reduced in size so as to avoid numerical artifacts resulting from the proximity of the target ROI and the stream function surface. The ROI was also designed to extend further into the patient's neck and was split in to two sub-regions. A uniform B1 field was desired in the first region (the "uniform ROI"), while zero field was desired in the second region (the "null ROI"). FIGS. 6A and 6B show these two ROIs. In particular, FIG. 6A is an example RF coil design surface shown in relation to a head-shaped ROI, where some ROI points sit outside of the RF coil design surface, and FIG. 6B is an RF coil design surface shown with modified "uniform" and "null" ROIs. As described above, the ROIs were selected in this manner in order to reduce the coil sensitivity in the poorly encoded neck region, thereby reducing the available signal that could alias into the image.

Figures 7A, 7B, 7C:
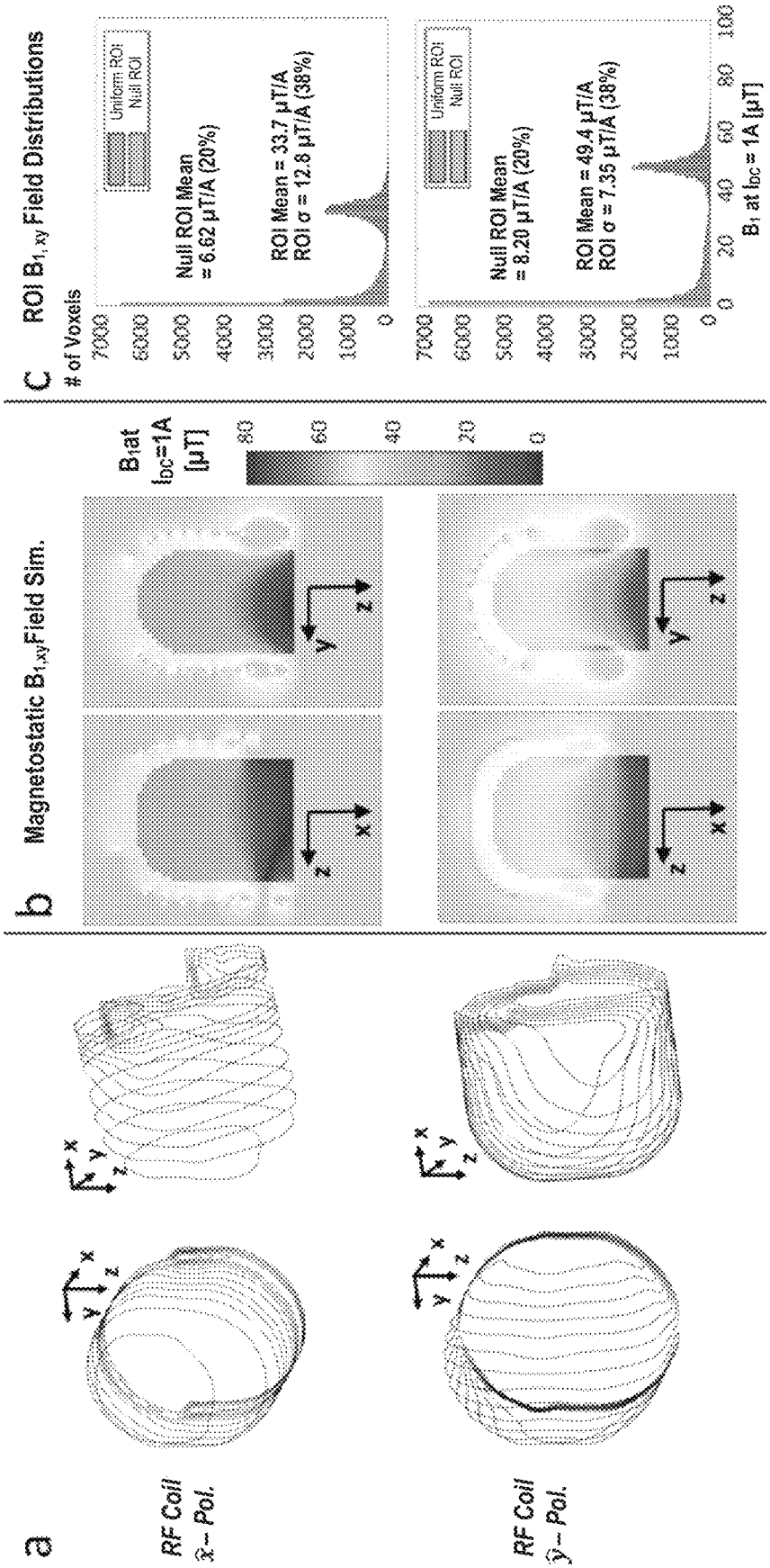
FIGS. 7A-7C show examples of steps in an optimized RF coil design.

The coil had y-axis linear polarization, resulting in a design that was inherently balanced about the center feed point. Alternatively, the coil can be designed with an x-polarized design produced with the same optimization, stream function surface, and target ROI/field. FIG. 7A shows an example of optimized coil windings for the x- and y-polarized coils, FIG. 7B shows their normalized simulated x-y component field maps ($B_{1,xy}=1$ at the isocenter for each coil), and FIG. 7C shows histograms showing the field in the "uniform" and "null" ROIs. The y-polarized coil field had a mean efficiency of 49.4 µT/A and a standard deviation of 7.35 µT/A (14.9%) within the "uniform" ROI, and produced 8.20 µT/TA (17%) in the "null" ROI. The x-polarized coil had a mean efficiency of 33.7 µT/A and a standard deviation of 12.8 µT/A (38%) within the "uniform" ROI, and produced 6.62 µT/A (20%) in the "null" ROI. The y-polarized design thus had a higher field efficiency, better uniform ROI field homogeneity, and a lower mean null ROI field.

Figure 8:
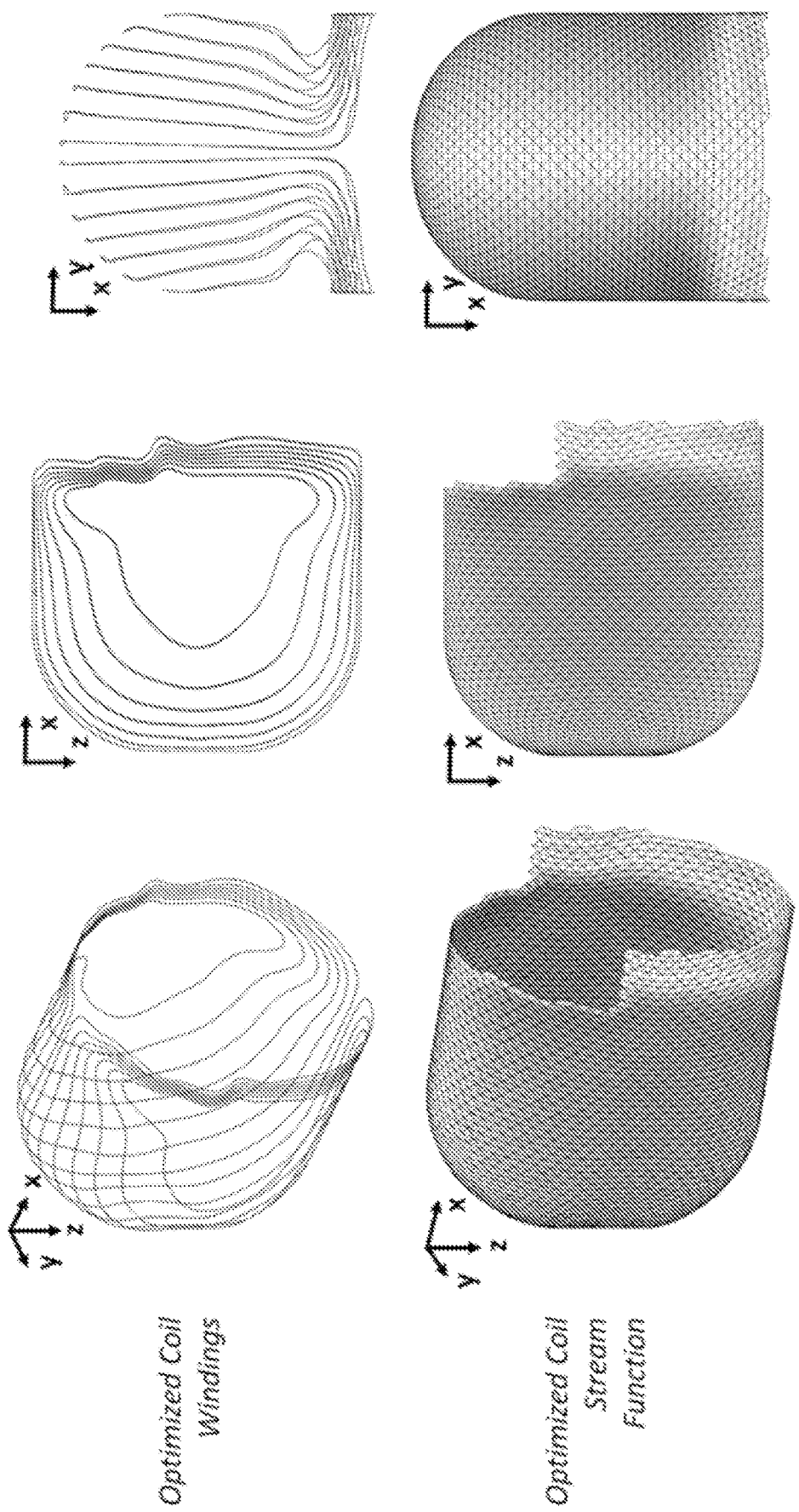
FIG. 8 shows an example of optimized y-polarized coil windings and a corresponding stream function.
Figure 9A:
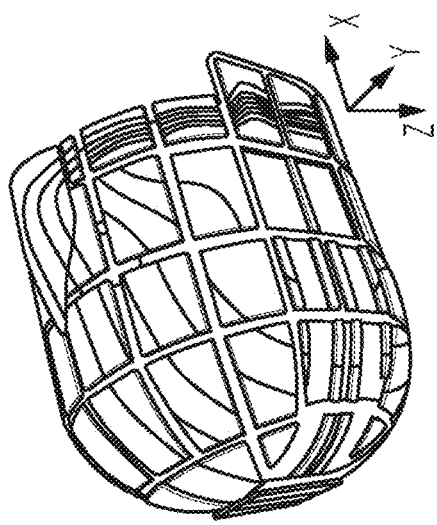
FIGS. 9A-9F show an example y-polarized RF coil and steps of its construction.
Figure 9B:
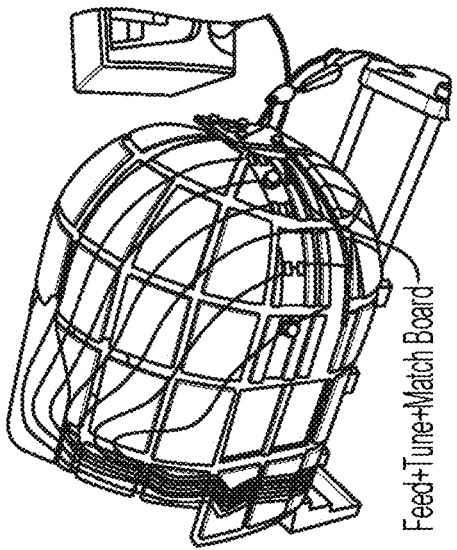
Figure 9C:
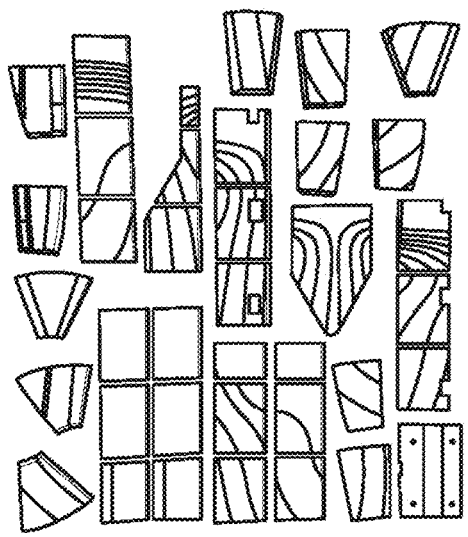
Figure 9D:
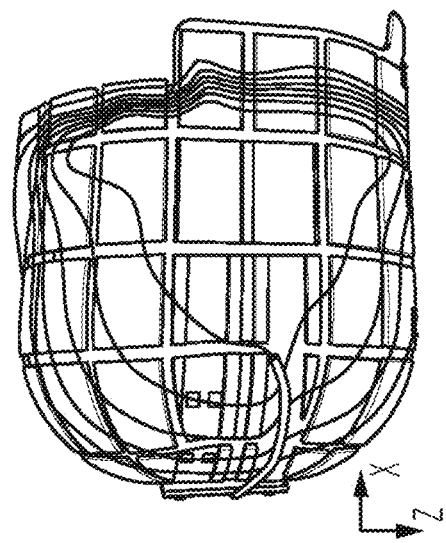
Figure 9E:
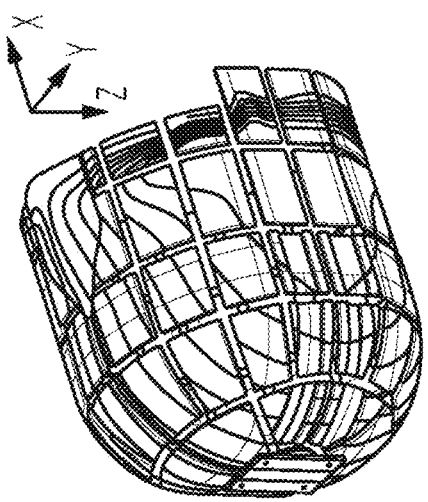
Figure 9F:
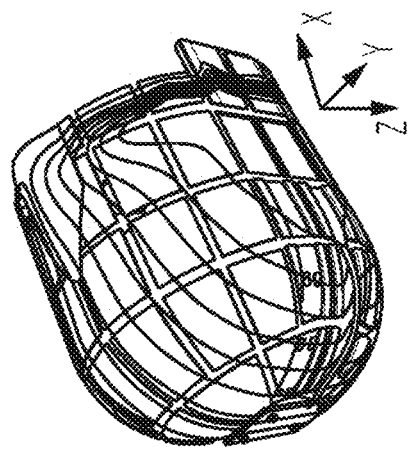

In this example, coil optimization implemented a BEM stream function approach. A parameter for the stream function optimization was tuned such that the resulting stream function looked smooth, and had >1 mm wire spacing when discretized with N=14 level sets. FIG. 8 shows the optimized coil stream function and windings An example process for designing and constructing an RF coil former is shown in relation to FIGS. 9A-9F. The RF coil former used in this example includes a plurality of tiles with etched grooves. The tiles were designed and etched in CAD (FIG. 9A), 3D-printed (FIG. 9B), and epoxied onto a helmet-shaped former (FIG. 9C). AWG36-strand Litz wire was then pressed into the grooves (FIGS. 9D and 9E). The coil had a routed circuit board in back for a coaxial cable feed and for tuning/matching circuits FIG. 9F. The wound coil inductance was measured at L=31 µH at f=1 kHz prior to tuning the coil. The coil winding was then split with four distributed tuning capacitors C≈360 pF in a balanced fashion. The coil was then tuned and matched on the feed board to f=3.09 MHz and 50Ω. The coil was initially tuned and matched in free space for field mapping, and was then tuned and matched inside the magnet and RF shield.

Figure 10:
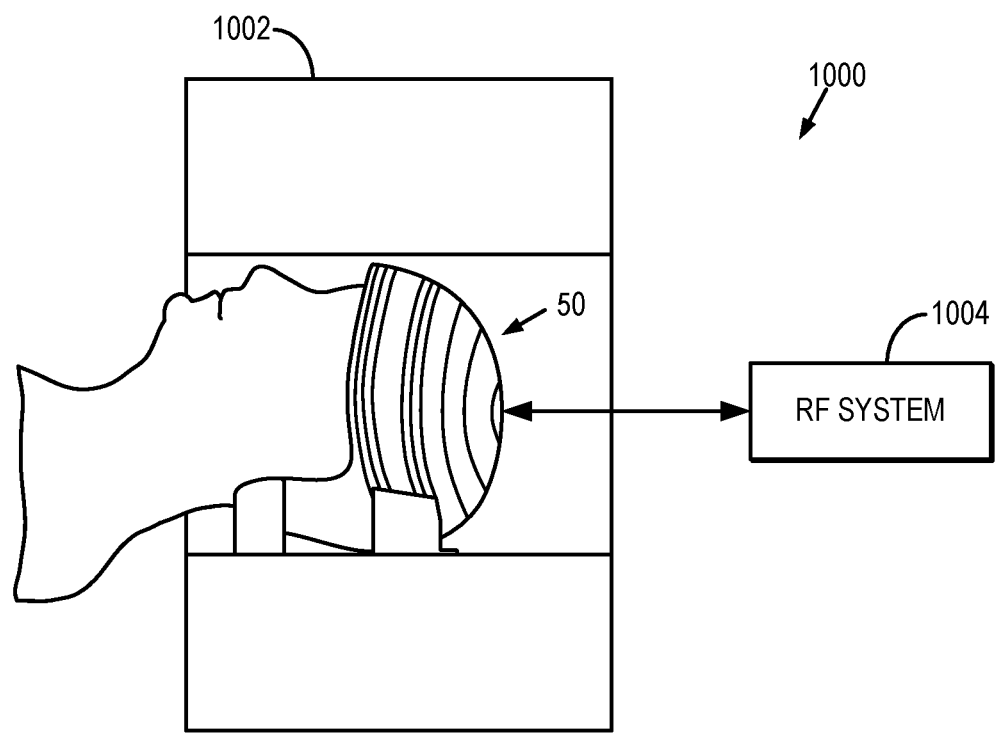
FIG. 10 is a block diagram of an example portable MRI system.

As shown in FIG. 10, a portable MRI scanner 1000 for human brain imaging can be based on a compact magnet 1002. For instance, the magnet can be a permanent magnet array, such as a sparse array of NdFeB rare-earth magnets in a Halbach cylinder configuration. Alternatively, electromagnet or superconducting magnets may also be used. In one non-limiting example, the average $B_0$ field is 80 mT and the Y-gradient is about 7.6 mT/m. A built-in gradient design reduces the magnet cost and weight and the system's acoustic noise and power/cooling needs (associated with a readout gradient coil in an inhomogeneous field).

An asymmetric RF coil 50 can be provided, which may be constructed as described above (e.g., as shown in FIGS. 1A-1C or FIGS. 2A and 2B). The asymmetric RF coil 50 connects to an RF system 1004 of the MRI system 1000, which is operable to control the transmit and receive functions of the RF coil 50.

Figure 11:
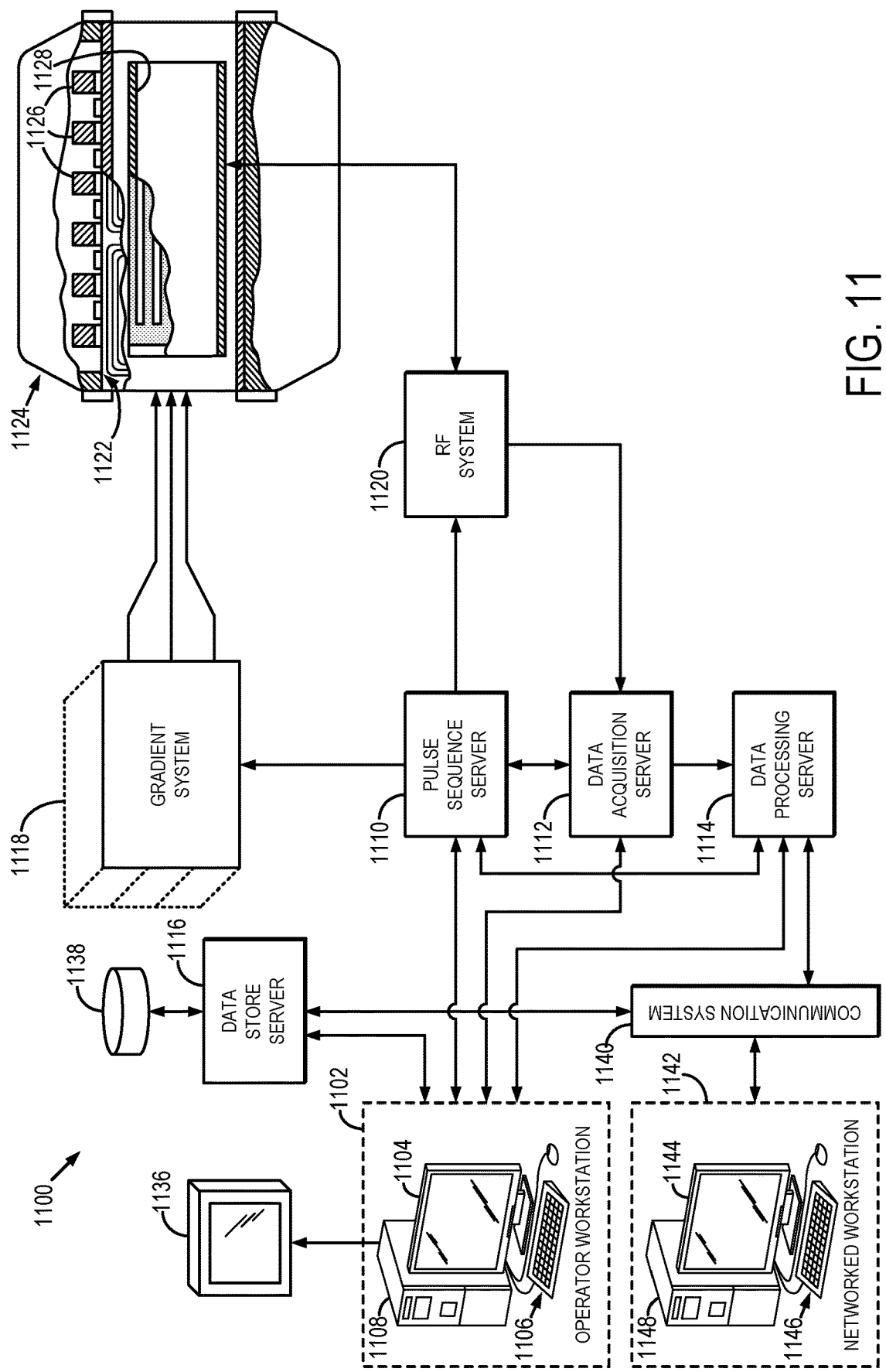
FIG. 11 is a block diagram of an example MRI system that can be configured as a portable and/or low-field MRI system.

Referring particularly now to FIG. 11, an example of an MRI system 1100 that can implement the methods described here is illustrated. The MRI system 1100 can be configured as a low-field MRI system, as a portable MRI system, or both. The MRI system 1100 includes an operator workstation 1102 that may include a display 1104, one or more input devices 1106 (e.g., a keyboard, a mouse), and a processor 1108. The processor 1108 may include a commercially available programmable machine running a commercially available operating system. The operator workstation 1102 provides an operator interface that facilitates entering scan parameters into the MRI system 1100. The operator workstation 1102 may be coupled to different servers, including, for example, a pulse sequence server 1110, a data acquisition server 1112, a data processing server 1114, and a data store server 1116. The operator workstation 1102 and the servers 1110, 1112, 1114, and 1116 may be connected via a communication system 1140, which may include wired or wireless network connections.

The pulse sequence server 1110 functions in response to instructions provided by the operator workstation 1102 to operate a gradient system 1118 and a radiofrequency ("RF") system 1120. Gradient waveforms for performing a prescribed scan are produced and applied to the gradient system 1118, which then excites gradient coils in an assembly 1122 to produce the magnetic field gradients $G_x$, $G_y$, and $G_z$ that are used for spatially encoding magnetic resonance signals. The gradient coil assembly 1122 forms part of a magnet assembly 1124 that includes a polarizing magnet 1126 and a whole-body RF coil 1128.

RF waveforms are applied by the RF system 1120 to the RF coil 1128, or a separate local coil (e.g., an asymmetric RF coil as described in the present disclosure) to perform the prescribed magnetic resonance pulse sequence. Responsive magnetic resonance signals detected by the RF coil 1128, or a separate local coil, are received by the RF system 1120. The responsive magnetic resonance signals may be amplified, demodulated, filtered, and digitized under direction of commands produced by the pulse sequence server 1110. The RF system 1120 includes an RF transmitter for producing a wide variety of RF pulses used in MRI pulse sequences. The RF transmitter is responsive to the prescribed scan and direction from the pulse sequence server 1110 to produce RF pulses of the desired frequency, phase, and pulse amplitude waveform. The generated RF pulses may be applied to the whole-body RF coil 1128 or to one or more local coils or coil arrays.

The RF system 1120 also includes one or more RF receiver channels. An RF receiver channel includes an RF preamplifier that amplifies the magnetic resonance signal received by the coil 1128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \tag{6}$$

and the phase of the received magnetic resonance signal may also be determined according to the following relationship:

$$\varphi = \tan^{-1}\left(\frac{Q}{I}\right). \tag{7}$$

The digitized magnetic resonance signal samples produced by the RF system 1120 are received by the data acquisition server 1112. The data acquisition server 1112 operates in response to instructions downloaded from the operator workstation 1102 to receive the real-time magnetic resonance data and provide buffer storage, so that data is not lost by data overrun. In some scans, the data acquisition server 1112 passes the acquired magnetic resonance data to the data processor server 1114. In scans that require information derived from acquired magnetic resonance data to control the further performance of the scan, the data acquisition server 1112 may be programmed to produce such information and convey it to the pulse sequence server 1110. For example, during pre-scans, magnetic resonance data may be acquired and used to calibrate the pulse sequence performed by the pulse sequence server 1110. The data acquisition server 1112 may, for example, acquire magnetic resonance data and processes it in real-time to produce information that is used to control the scan.

The data processing server 1114 receives magnetic resonance data from the data acquisition server 1112 and processes the magnetic resonance data in accordance with instructions provided by the operator workstation 1102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 1114 are conveyed back to the operator workstation 1102 for storage. Real-time images may be stored in a data base memory cache, from which they may be output to operator display 1102 or a display 1136. Batch mode images or selected real time images may be stored in a host database on disc storage 1138. When such images have been reconstructed and transferred to storage, the data processing server 1114 may notify the data store server 1116 on the operator workstation 1102. The operator workstation 1102 may be used by an operator to archive the images, produce films, or send the images via a network to other facilities.

The MRI system 1100 may also include one or more networked workstations 1142. For example, a networked workstation 1142 may include a display 1144, one or more input devices 1146 (e.g., a keyboard, a mouse), and a processor 1148. The networked workstation 1142 may be located within the same facility as the operator workstation 1102, or in a different facility, such as a different healthcare institution or clinic.

The networked workstation 1142 may gain remote access to the data processing server 1114 or data store server 1116 via the communication system 1140. Accordingly, multiple networked workstations 1142 may have access to the data processing server 1114 and the data store server 1116. In this manner, magnetic resonance data, reconstructed images, or other data may be exchanged between the data processing server 1114 or the data store server 1116 and the networked workstations 1142, such that the data or images may be remotely processed by a networked workstation 1142.

Figure 12:
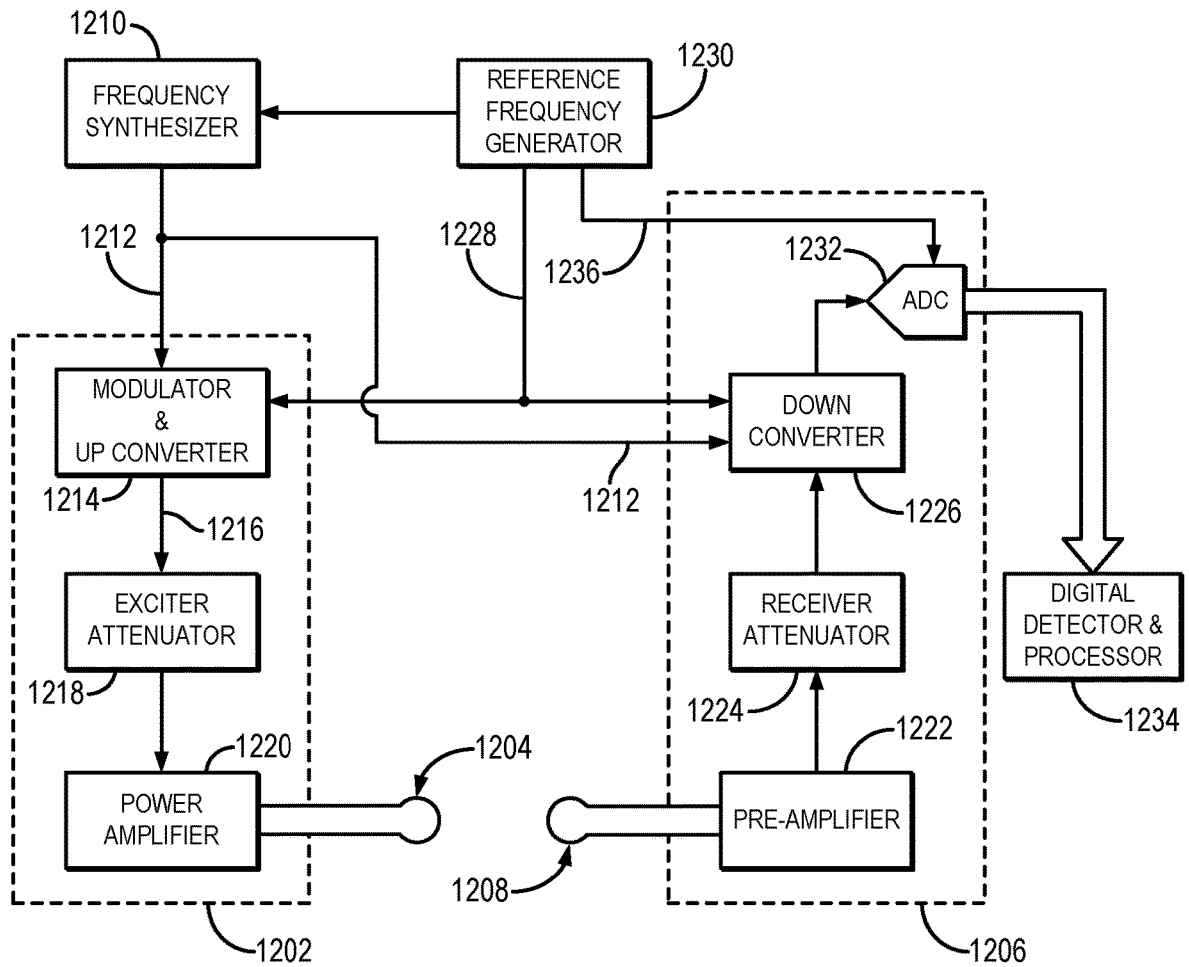
FIG. 12 is a block diagram of an example RF system that can be implemented with a portable and/or low-field MRI system.

As shown in FIG. 11, the radiofrequency ("RF") system 1120 may be connected to the whole body RF coil 1128, or, as shown in FIG. 12, a transmission channel 1202 of the RF system 1120 may connect to a RF transmission coil 1204 and a receiver channel 1206 may connect to a separate RF receiver coil 1208. Often, the transmission channel 1202 is connected to the whole body RF coil 1128 and each receiver section is connected to a separate local RF coil.

Referring particularly to FIG. 12, the RF system 1120 includes a transmission channel 1202 that produces a prescribed RF excitation field. The base, or carrier, frequency of this RF excitation field is produced under control of a frequency synthesizer 1210 that receives a set of digital signals from the pulse sequence server 1110. These digital signals indicate the frequency and phase of the RF carrier signal produced at an output 1212. The RF carrier is applied to a modulator and up converter 1214 where its amplitude is modulated in response to a signal, R(t), also received from the pulse sequence server 1110. The signal, R(t), defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 1216 is attenuated by an exciter attenuator circuit 1218 that receives a digital command from the pulse sequence server 1110. The attenuated RF excitation pulses are then applied to a power amplifier 1220 that drives the RF transmission coil 1204.

The MR signal produced by the subject is picked up by the RF receiver coil 1208 and applied through a preamplifier 1222 to the input of a receiver attenuator 1224. The receiver attenuator 1224 further amplifies the signal by an amount determined by a digital attenuation signal received from the pulse sequence server 1110. The received signal is at or around the Larmor frequency, and this high frequency signal is down converted in a two-step process by a down converter 1226. The down converter 1226 first mixes the MR signal with the carrier signal on line 1212 and then mixes the resulting difference signal with a reference signal on line 1228 that is produced by a reference frequency generator 1230. The down converted MR signal is applied to the input of an analog-to-digital ("A/D") converter 1232 that samples and digitizes the analog signal. The sampled and digitized signal is then applied to a digital detector and signal processor 1234 that produces 16-bit in-phase (I) values and 16-bit quadrature (Q) values corresponding to the received signal. The resulting stream of digitized I and Q values of the received signal are output to the data acquisition server 1112. In addition to generating the reference signal on line 1228, the reference frequency generator 1230 also generates a sampling signal on line 1236 that is applied to the A/D converter 1232.

The present disclosure has described one or more preferred embodiments, and it should be appreciated that many equivalents, alternatives, variations, and modifications, aside from those expressly stated, are possible and within the scope of the invention.

The invention claimed is:

1. A radio frequency (RF) coil system for performing a magnetic resonance imaging (MRI) process using an MRI system, the RF coil system comprising:
    a substrate configured to follow a contour of a portion of a subject to be imaged by the MRI system; and
    at least one RF coil coupled to the substrate and forming an asymmetrical three-dimensional spiral pattern extending over the substrate, wherein the asymmetrical three-dimensional spiral pattern includes adjacent portions of the at least one RF coil that are non-uniformly spaced apart over the substrate, wherein the three-dimensional spiral pattern is arranged to produce a homogeneous target field within a region-of-interest and to produce a transverse magnetic field that reduces a sensitivity of the at least one RF coil outside of the region-of-interest.

2. The RF coil system of claim 1, wherein the asymmetrical three-dimensional spiral pattern comprises a variable turn density.

3. The RF coil system of claim 1, wherein the at least one RF coil is sized to image a periphery of the subject.

4. The RF coil system of claim 1, wherein the at least one RF coil is configured to operate as a transmit and receive coil.

5. The RF coil system of claim 1, wherein the substrate forms a helmet and the portion of the subject is a head, such that the helmet is configured to contour the head of the subject.

6. The RF coil system of claim 5, wherein the at least one RF coil is configured to spiral out from a center aligned with a crown of the head of the subject to a perimeter encircling the head of the subject.

7. The RF coil system of claim 5, wherein the asymmetrical three-dimensional spiral pattern comprises a higher turn density at a base of the helmet than at an apex of the helmet.

8. The RF coil system of claim 1, wherein the substrate is manufactured using an additive manufacturing process.

9. The RF coil system of claim 8, wherein the substrate is manufactured using a three-dimensional (3D) printing process.

10. The RF coil system of claim 1, wherein the substrate includes a series of grooves in an outer surface of the substrate, and wherein the at least one coil is coupled to the grooves formed in the outer surface of the substrate.

11. A single channel radio frequency (RF) coil configured for a portion of human anatomy, the single channel RF coil comprising:
    a conductor arranged in a three-dimensional asymmetrical geometry about a region-of-interest, wherein the conductor is arranged with a wire pattern to produce a transverse magnetic field that reduces sensitivity outside of the region-of-interest, and wherein, when the single channel RF coil is operated in conjunction with performing magnetic resonance of the portion of the human anatomy of a subject, the conductor is configured to produce and detect magnetic fields within the region-of-interest and substantially parallel to a longitudinal axis of the subject's body.

12. The single channel RF coil of claim 11, wherein the conductor is arranged in an asymmetrical spiral geometry.

13. The single channel RF coil of claim 12, wherein the asymmetrical spiral geometry comprises a variable turn density.

14. The single channel RF coil of claim 12, wherein the asymmetrical spiral geometry comprises a spiral having at least some adjacent portions with a non-uniform spacing therebetween.

15. The single channel RF coil of claim 11 configured as a head coil comprising a substrate formed to accommodate the subject's head, wherein the conductor is arranged in the three-dimensional asymmetrical geometry over a surface of the substrate.

16. The single channel RF coil of claim 15, wherein the conductor is arranged over at least a hemisphere of the substrate.

17. The single channel RF coil of claim 11, wherein the conductor is formed by a wire arranged in the three-dimensional asymmetrical geometry.

18. The single channel RF coil of claim 17, wherein the wire is a single-strand wire.

19. The single channel RF coil of claim 18, wherein the wire is a Litz wire.

20. The single channel RF coil of claim 11, wherein the conductor is arranged in the three-dimensional asymmetrical geometry such that the conductor forms at least 10 turns and such that at least some adjacent portions of the conductor are spaced apart with a non-uniform spacing therebetween.

\* \* \* \* \*